(12) United States Patent
Thenuwara et al.

(10) Patent No.: US 9,056,196 B2
(45) Date of Patent: Jun. 16, 2015

(54) COCHLEAR ELECTRODE ARRAY

(75) Inventors: Chuladatta Thenuwara, Castaic, CA (US); Timothy Beerling, San Francisco, CA (US)

(73) Assignee: ADVANCED BIONICS, LLC, Valencia, CA (US)

( * ) Notice: Subject to any disclaimer, the term of this patent is extended or adjusted under 35 U.S.C. 154(b) by 34 days.

(21) Appl. No.: 13/516,982

(22) PCT Filed: Dec. 14, 2010

(86) PCT No.: PCT/US2010/060306
§ 371 (c)(1),
(2), (4) Date: Aug. 14, 2012

(87) PCT Pub. No.: WO2011/075480
PCT Pub. Date: Jun. 23, 2011

(65) Prior Publication Data
US 2012/0296405 A1 Nov. 22, 2012

Related U.S. Application Data

(60) Provisional application No. 61/288,201, filed on Dec. 18, 2009.

(51) Int. Cl.
*A61N 1/05* (2006.01)
*A61N 1/36* (2006.01)

(52) U.S. Cl.
CPC ......... *A61N 1/0541* (2013.01); *Y10T 29/49204* (2015.01); *A61N 1/36032* (2013.01)

(58) Field of Classification Search
CPC .................. A61N 1/0541; A61N 1/36032
USPC ............... 607/55–57, 116, 136–137; 600/379
See application file for complete search history.

(56) References Cited

U.S. PATENT DOCUMENTS

| 4,686,765 A | 8/1987 | Byers et al. |
|---|---|---|
| 4,819,647 A | 4/1989 | Byers et al. |
| 6,070,105 A * | 5/2000 | Kuzma .......................... 607/137 |
| 6,374,143 B1 | 4/2002 | Berrang et al. |

(Continued)

FOREIGN PATENT DOCUMENTS

| EP | 1839626 A1 | 10/2007 |
|---|---|---|
| WO | 03041092 A1 | 5/2003 |
| WO | 2009065127 | 5/2009 |

OTHER PUBLICATIONS

Lu et al., Activated iridium oxide films fabricated by asymmetric pulses for electrical neural microstimulation and recording. Electrochemistry communications. vol. 10, Issue 5, May 2008, pp. 778-782.

*Primary Examiner* — Catherine Voorhees
(74) *Attorney, Agent, or Firm* — Steven L. Nichols; Van Cott, Bagley, Cornwall & McCarthy P.C.

(57) ABSTRACT

A cochlear lead includes a plurality of electrode assemblies partially embedded in a flexible body configured to stimulate an auditory nerve from within a cochlea. Each of the electrode assemblies includes a flexible electrically conductive material forming a plurality of support structures and an electrode pad attached a support structure, the electrode pad having a surface that is configured to be exposed to cochlear tissue and fluids and has a charge transfer to the cochlear tissue and fluids that is higher than the flexible electrically conductive material.

21 Claims, 14 Drawing Sheets

(56) References Cited

U.S. PATENT DOCUMENTS

| | | |
|---|---|---|
| 6,757,970 B1 | 7/2004 | Kuzma et al. |
| 6,862,805 B1 * | 3/2005 | Kuzma et al. ............... 29/858 |
| 6,974,533 B2 | 12/2005 | Zhou |
| 7,294,409 B2 | 11/2007 | Lye et al. |
| 8,489,202 B2 * | 7/2013 | Zhou et al. ............... 607/115 |
| 2004/0127968 A1 | 7/2004 | Kuzma |
| 2005/0021118 A1 * | 1/2005 | Genau et al. ............... 607/116 |
| 2006/0247754 A1 * | 11/2006 | Greenberg et al. ............ 607/137 |
| 2007/0293749 A1 | 12/2007 | Zhou et al. |
| 2009/0030483 A1 | 1/2009 | Risi et al. |
| 2009/0306745 A1 * | 12/2009 | Parker et al. ............... 607/57 |
| 2011/0071596 A1 | 3/2011 | Kara et al. |
| 2011/0126410 A1 | 6/2011 | Capcelea et al. |
| 2011/0130815 A1 | 6/2011 | Gibson et al. |

* cited by examiner

COCHLEAR ELECTRODE ARRAY

RELATED DOCUMENTS

The present application claims the priority under 35 U.S.C. 119(a)-(d) or (f) and under C.F.R. 1.55(a) of previous International Patent Application No. PCT/US2010/060306, filed Dec. 14, 2010, entitled "Cochlear Electrode Array" which claims the benefit under 35 U.S.C. §119(e) of U.S. Provisional Application No. 61/288,201, entitled "Cochlear Electrode Array" filed Dec. 18, 2009, which applications are incorporated herein by reference in their entirety.

BACKGROUND

In human hearing, hair cells in the cochlea respond to sound waves and produce corresponding auditory nerve impulses. These nerve impulses are then conducted to the brain and perceived as sound.

Damage to the hair cells results in loss of hearing because sound energy which is received by the cochlea is not transduced into auditory nerve impulses. This type of hearing loss is called sensorineural deafness. To overcome sensorineural deafness, cochlear implant systems, or cochlear prostheses, have been developed. These cochlear implant systems bypass the defective or missing hair cells located in the cochlea by presenting electrical stimulation directly to the ganglion cells in the cochlea. This electrical stimulation is supplied by an electrode array which is implanted in the cochlea. The ganglion cells then generate nerve impulses which are transmitted through the auditory nerve to the brain. This leads to the perception of sound in the brain and provides at least partial restoration of hearing function.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Figure 1:
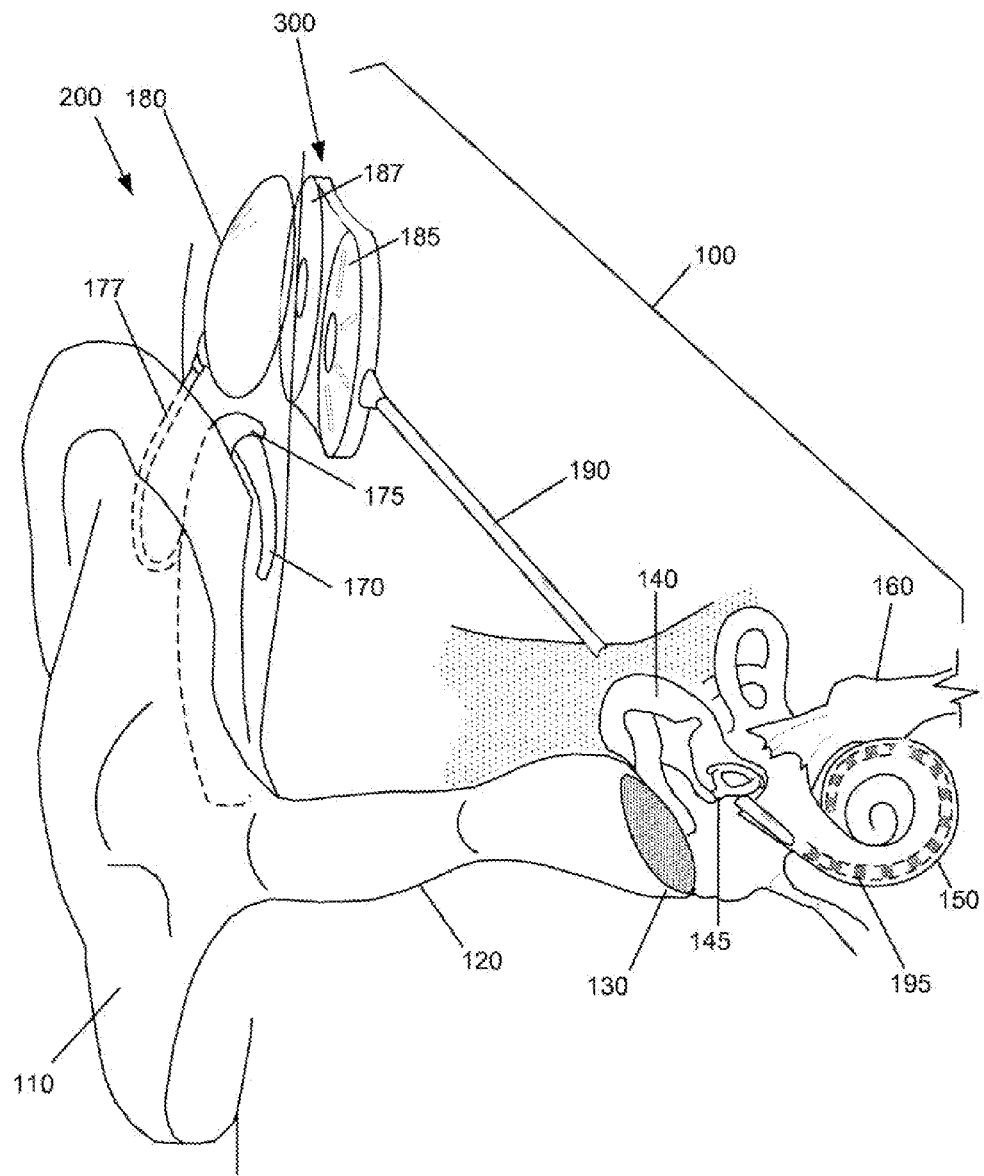
FIG. 1 is a diagram showing an illustrative cochlear implant system in use, according to one embodiment of principles described herein.

As mentioned above, individuals with hearing loss can be assisted by a number of hearing devices, including cochlear implants. Cochlear implants are made up of both external and implanted components. The external components detect environmental sounds and convert the sounds into acoustic signals. These acoustic signals are separated into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex. An electrode array is inserted into the cochlea and has a number of electrodes which corresponded to the tonotopic organization of the cochlea. Electrical signals are transmitted through a wire to each of the electrodes in the electrical array. When an electrode is energized, it transfers the electrical charge to the surrounding fluids and tissues. This triggers the ganglion cells to generate nerve impulses which are conveyed through the auditory nerve to the brain and perceived as sound.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

A cochlear electrode array is a thin, elongated, flexible carrier containing several longitudinally disposed and separately connected stimulating electrode contacts, conventionally numbering about 6 to 30. According to one illustrative embodiment, the electrode array may be constructed out of biocompatible silicone, platinum-iridium wires, and platinum electrodes. This gives the distal portion of the lead the flexibility to curve around the helical interior of the cochlea.

To place the electrode array into the cochlea, the electrode array may be inserted through a cochleostomy or via a surgical opening made in the round window of the cochlea. The electrode array is inserted through the opening into the scala tympani, one of the three parallel ducts that make up the spiral-shaped cochlea. The electrode array is typically inserted into the scala tympani duet in the cochlea to a depth of about 13 to 30 mm.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of such current. Consequently, stimulation at one contact site tends to selectively activate those spiral ganglion cells and their auditory nerve fibers that are closest to that contact site.

Improved charge transfer from the surface of the electrode to the surrounding fluid and tissues reduces impedances and improves battery life of the cochlear implant system. While smooth platinum is a reliable stimulating surface for cochlear implants, it has been discovered that there are other biocompatible materials and surface structures that have better charge transfer between the electrode and surrounding tissues. One of these materials is activated iridium. To activate iridium, the iridium surface undergoes a number of electrochemical cycles in a water-based electrolyte to develop an "activated" iridium oxide surface that is superior to platinum for charge transfer.

However, iridium is a relatively brittle material compared to platinum. As a consequence, iridium may be less suitable for other electrode manufacturing steps which are used to form some types of cochlear electrode arrays. The new techniques and structures described below maximize the charge transfer of the electrode surface while maintaining the manufacturability of the electrode arrays. These automated or semi-automated techniques also minimize part-to-part variability and defects which result from less controlled manual processes.

FIG. 1 is a diagram showing one illustrative embodiment of a cochlear implant system (100) having a cochlear implant (300) with an electrode array (195) that is surgically placed within the patient's auditory system. Ordinarily, sound enters the external ear, or pinna, (110) and is directed into the auditory canal (120) where the sound wave vibrates the tympanic membrane (130). The motion of the tympanic membrane is amplified and transmitted through the ossicular chain (140), which consists of three bones in the middle ear. The third bone of the ossicular chain (140), the stirrup (145), contacts the outer surface of the cochlea (150) and causes movement of the fluid within the cochlea. Cochlear hair cells respond to the fluid-borne vibration in the cochlea (150) and trigger neural electrical signals that are conducted from the cochlea to the auditory cortex by the auditory nerve (160).

As indicated above, the cochlear implant (300) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

As discussed above, the cochlear implant (300) does not amplify sound, but works by directly stimulating the auditory nerve (160) with electrical impulses representing the ambient acoustic sound. Cochlear prosthesis typically involves the implantation of electrodes into the cochlea. The cochlear implant operates by direct electrical stimulation of the auditory nerve cells, bypassing the defective cochlear hair cells that normally transduce acoustic energy into electrical energy.

External components (200) of the cochlear implant system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by electromagnetic transmission. In some cochlear implant systems, the transmitter (180) is held in place by magnetic interaction with a magnet in the center of the underlying antenna (187).

The components of the cochlear implant (300) include an internal processor (185), an antenna (187), and a cochlear lead (190) which terminates in an electrode array (195). The internal processor (185) and antenna (187) are secured beneath the user's skin, typically above and behind the pinna (110). The antenna (187) receives signals and power from the transmitter (180). The internal processor (185) receives these signals and performs one or more operations on the signals to generate modified signals. These modified signals are then sent along a number of delicate wires which pass through the cochlear lead (190). These wires are individually connected to the electrodes in the electrode array (195). The electrode array (195) is implanted within the cochlea (150) and provides electrical stimulation to the auditory nerve (160).

The cochlear implant (300) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
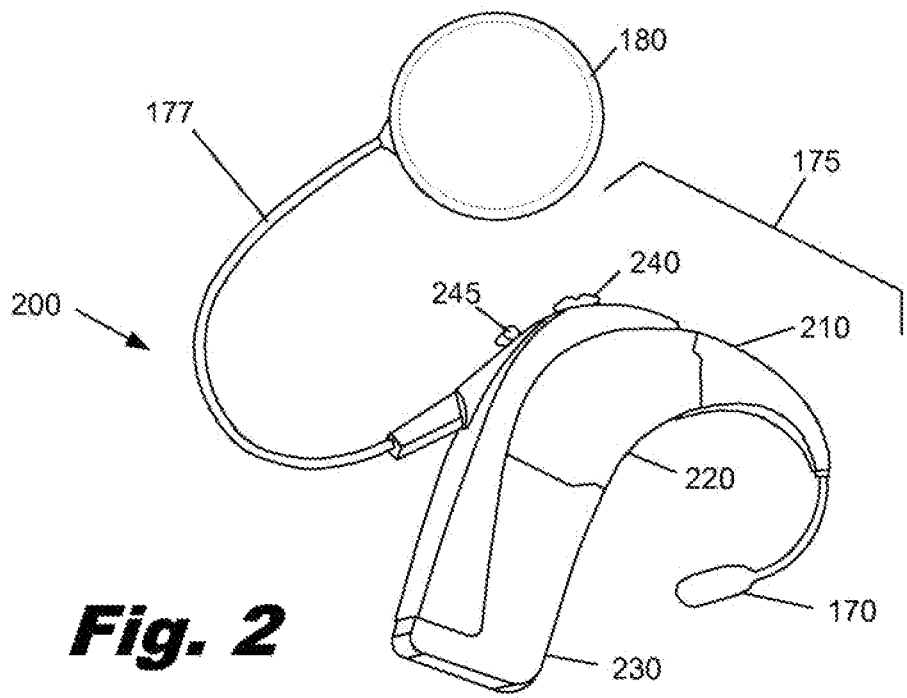
FIG. 2 is a diagram showing external components of an illustrative cochlear implant system, according to one embodiment of principles described herein.

FIG. 2 is an illustrative diagram showing a more detailed view of the external components (200) of one embodiment of a cochlear implant system. External components (200) of the cochlear implant system include a BTE unit (175), which comprises a microphone (170), an ear hook (210), a sound processor (220), and a battery (230), which may be rechargeable. The microphone (170) picks up sound from the environment and converts it into electrical impulses. As discussed above, the sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the cochlear implant by electromagnetic transmission.

Figure 3:
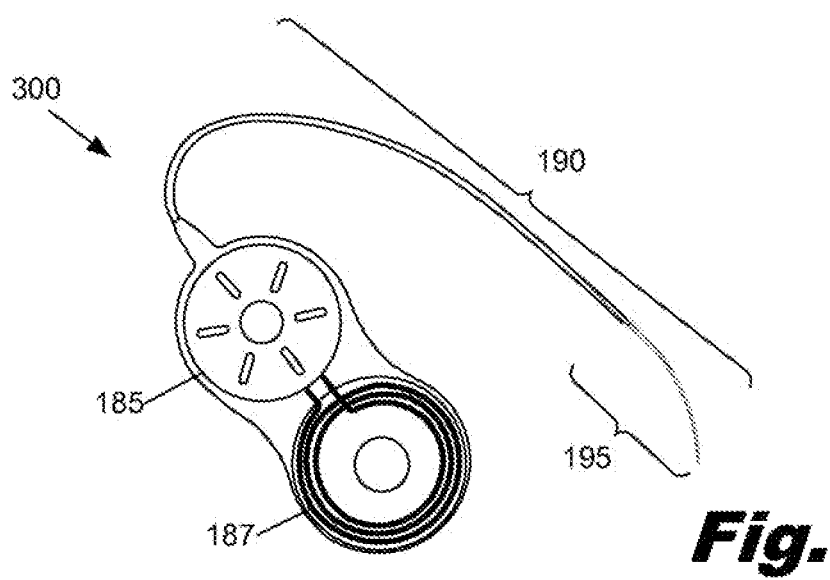
FIG. 3 is a diagram showing the internal components of an illustrative cochlear implant system, according to one embodiment of principles described herein.

FIG. 3 is an illustrative diagram showing one embodiment of a cochlear implant (300), including an internal processor (185), an antenna (187), and a cochlear lead (190) having an electrode array (195). The cochlear implant (300) is surgically implanted such that the electrode array (195) is internal to the cochlea, as shown in FIG. 1. The internal processor (185) and antenna (187) are secured beneath the user's skin, typically above and behind the pinna (110, FIG. 1), with the cochlear lead (190) connecting the internal processor (185) to the electrode array (195) within the cochlea. As discussed above, the antenna (187) receives signals from the transmitter (180) and sends the signals to the internal processor (185). The internal processor (185) modifies the signals and passes them along the appropriate wires to activate one or more of the electrodes within the electrode array (195). This provides the user with sensory input that is a representation of external sound waves sensed by the microphone (170).

Figure 4:
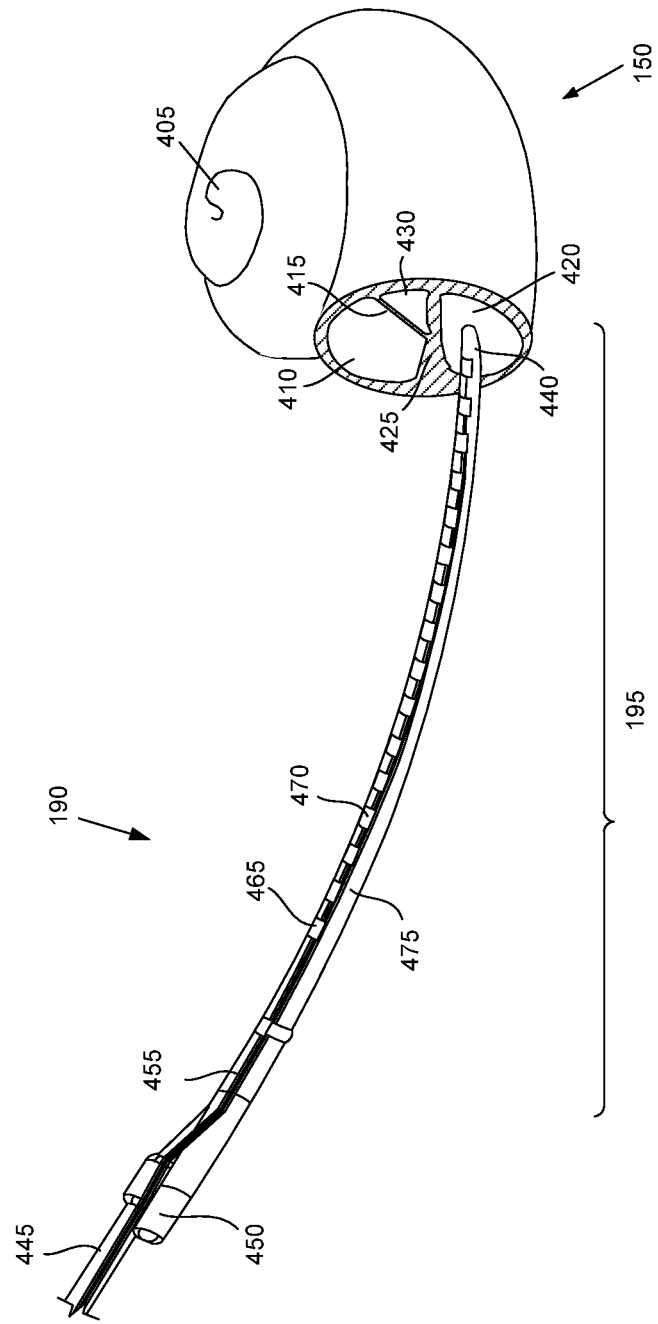
FIG. 4 is a perspective view of an illustrative electrode array being inserted into a cochlea, according to one embodiment of principles described herein.

FIG. 4 is a partially cut away perspective view of a cochlea (150) and shows an illustrative electrode array (195) being inserted into the cochlea (150). The primary structure of the cochlea is a hollow, helically coiled, tubular bone (405), similar to a nautilus shell. The coiled tube is divided through most of its length into three fluid-filled spaces (scalae). The scala vestibuli (410) is partitioned from the scala media (430) by Reissner's membrane (415) and lies superior to it. The scala tympani (420) is partitioned from the scala media (430) by the basilar membrane (425) and lies inferior to it. A typical human cochlea includes approximately two and a half helical turns of its various constituent channels. The cochlear lead (190) is inserted into one of the scalae, typically the scalae tympani (420), to bring the individual electrodes into close proximity with the tonotopically organized nerves.

The illustrative cochlear lead (190) includes a lead body (445). The lead body (445) connects the electrode array (195) to the internal processor (185, FIG. 3). A number of wires (455) pass through the lead body (445) to bring electrical signals from the internal processor (185, FIG. 3) to the electrode array (195). According to one illustrative embodiment, at the junction of the electrode array (195) to the lead body (445) is a molded silicone rubber feature (450). The feature (450) can serve a variety of functions, including, but not limited to, providing a structure which can be gripped by an insertion tool, providing a visual indicator of how far the cochlear lead (190) has been inserted, and securing the electrode array (195) within the cochlea.

The wires (455) that conduct electrical signals are connected to the electrodes (465, 470) within the electrode array (195). For example, electrical signals which correspond to a low frequency sound may be communicated via a first wire to an electrode near the tip (440) of the electrode array (195). Electrical signals which correspond to a high frequency sound may be communicated by a second wire to an electrode (465) near the base of the electrode array (195). According to one illustrative embodiment, there may be one wire (455) for each electrode within the electrode array (195). The internal processor (185, FIG. 3) may then control the electrical field generated by each electrode individually. For example, one electrode may be designated as a ground electrode. The remainder of the electrodes may then generate electrical fields which correspond to various frequencies of sound. Additionally or alternatively, adjacent electrodes may be paired, with one electrode serving as a ground and the other electrode being actively driven to produce the desired electrical field.

According to one illustrative embodiment, the wires (455) and portions of the electrodes (470) are encased in a flexible body (475). The flexible body (475) may be formed from a variety of biocompatible materials, including, but not limited to medical grade silicone rubber. The flexible body (475) secures and protects the wires (455) and electrodes (465, 470). The flexible body (475) allows the electrode array (195) to bend and conform to the geometry of the cochlea.

Figure 5:
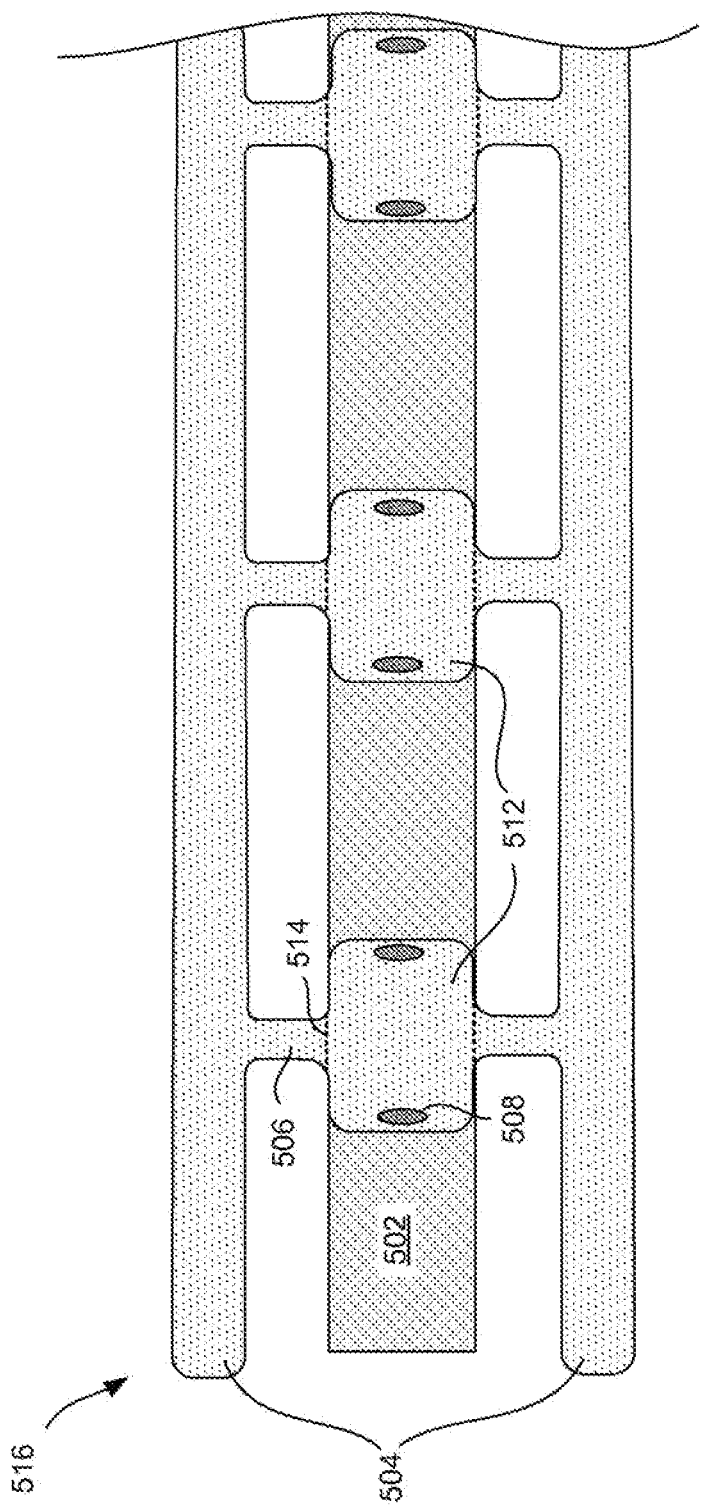
FIG. 5 is a top view of a patterned sheet of electrochemically activated material attached to a sacrificial substrate, according to one embodiment of principles described herein.

FIG. 5 is a diagram of a material which exhibits high charge transfer to cochlear tissues. This material has been formed into a tethered set of electrode pads (516) and attached to an underlying sacrificial substrate (502). As used in the specification and appended claims, the term "forming" or "formed" includes a wide variety of subtractive, additive, or transformative processes, including but not limited to, mechanical removal of material, laser cutting, electrical discharge machining (EDM), photolithographic techniques and etching, electron beam machining, abrasive flow machining, casting, extruding, stamping, imprinting, molding, and other suitable processes. According to one illustrative embodiment, a number of generally rectangular electrode pads (512) have been formed along the center of the patterned high charge transfer material. The electrode pads (512) may have a number of other shapes including, but not limited to circular, oval, square, or trapezoidal. Further, the shape and size of the electrode pads may vary throughout the tethered set (516). In some embodiments, it may be desirable to form the sheet into shapes with at least some three dimensional curvature.

Each electrode pad (512) is tethered to rails (504) by two tethers (506). As used in the specification and appended claims, the term "tether" or "tethered" refers to a connection between an electrode and the structure that holds the electrodes in a fixed spatial relationship with other electrodes. Ordinarily, the tether (506) has a relatively small cross-section compared to the electrode pad (512) and connects the perimeter of the electrode pad (512) and the rails (504). The tethers (506) can hold the electrode pads (512) rigidly in place to completely fix the electrode spacing or semi-rigidly such that they are close to their final spacing and can be put into an alignment fixture to adjust the final spacing. In one embodiment, tether widths are between 50 and 250 microns and lengths of the tethers are between 100 and 500 microns. According to one illustrative embodiment, the electrode pads (512) and tethers (506) are formed from a single sheet of high charge transfer material.

According to one illustrative embodiment, the high charge transfer material may be iridium or an iridium alloy. For example, iridium could be activated by exposing it to a number of electrochemical cycles in a water-based electrolyte to develop an activated iridium oxide surface. This activated iridium oxide surface has a higher area and greater charge transfer characteristics than the underlying iridium material. The electrochemical activation of the iridium surface could be performed before or after the assembly of the electrode array.

The high charge transfer material may be patterned using a number of techniques including, but not limited to, short pulse laser micromachining techniques. As used in the specification and appended claims, the term "short pulse" means pulses less than a nanosecond, such as in the femtosecond to hundreds of picosecond range. A variety of lasers can be used. For example, very short pulse laser machining may be performed using a picosecond laser, at UV, visible, or IR wavelengths. These very short pulse lasers can provide superior micromachining compared with longer pulse lasers. The very short pulse lasers ablate portions of the material without significant transfer of heat to surrounding areas. This allows the very short pulse lasers to machine fine details and leaves the unablated material in essentially its original state.

The set (516) of tethered electrode pads (512) is fixed to a sacrificial substrate (502). According to one illustrative embodiment, the sacrificial substrate (502) may be an iron strip which is approximately the width of the electrode pads (512) and at least as long as the tethered set (516) of electrode pads. The tethered set (516) of electrode pads may be attached to the sacrificial substrate (502) in a variety of ways, including resistance welding or laser welding. One or more weld joints (508) can be made for each electrode pad (512). The spacing of the electrode pads (512) is initially maintained by the tethers (506). The tethers (506) are cut after the welds (508) are formed. According to one illustrative embodiment, the tethers (506) are cut at or near the dotted lines (514). After the tethers (506) are cut, the iron strip (502) maintains the desired electrode pad (512) spacing and orientation.

Figure 6:
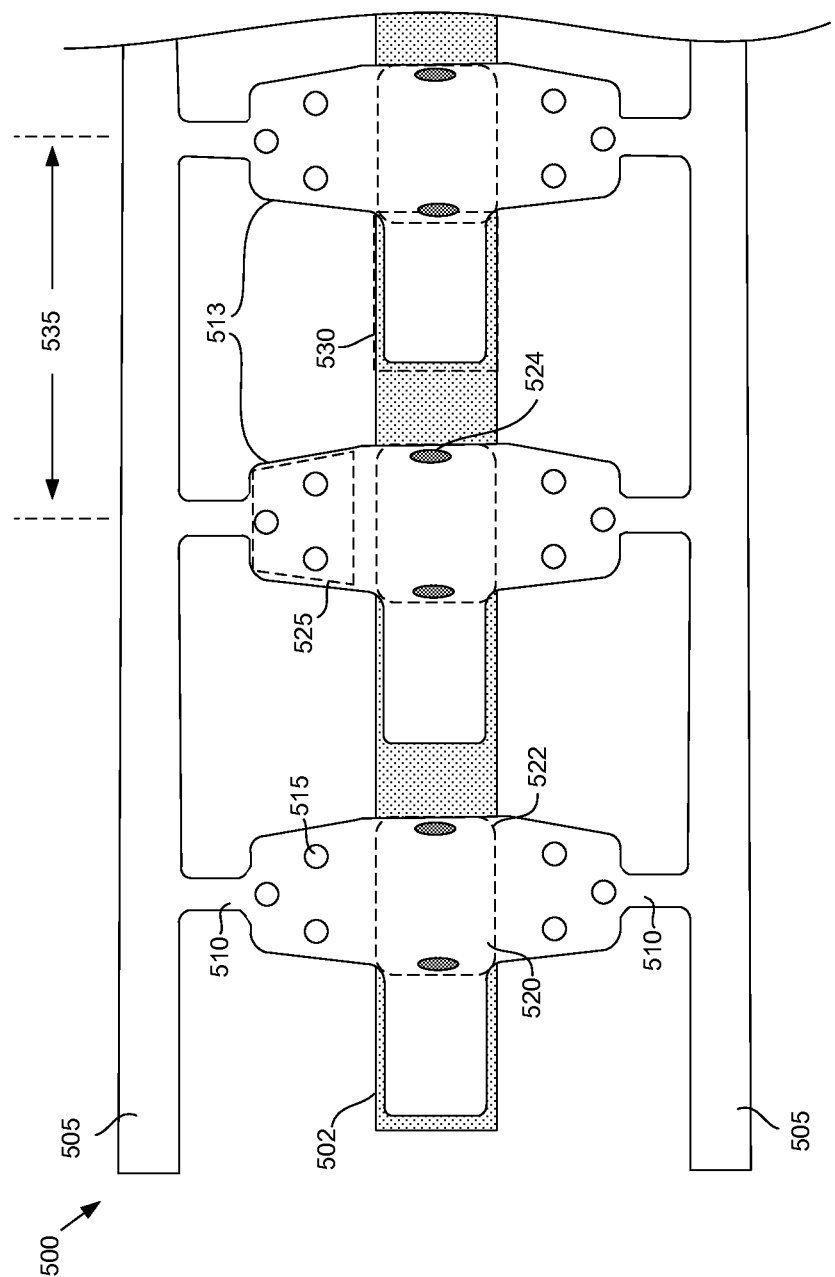
FIG. 6 is a top view of a patterned sheet of flexible conductive material which is attached to underlying electrode pads, according to one embodiment of principles described herein.

FIG. 6 is a diagram of an illustrative tethered set (500) of winged tabs (513) which have been machined from a flexible electrically conductive material. As used in the specification and appended claims, the term "flexible material" or "flexible electrically conductive material" refers to a material with a thickness of 20 to 1000 microns which can be creased or folded at greater than 90 degree angles without significant cracking or other failure at the crease or fold. For example, some platinum and platinum alloys are flexible materials according to this definition. According to one illustrative embodiment, the tethered set (500) of winged tabs includes a series of winged tabs (513) which are machined from a platinum or platinum alloy foil using short pulse laser machining. For example, the sheet material may be between 20 and 50 micron thick platinum or platinum alloy (such as platinum/iridium having up to 20% iridium).

As discussed above, after the tethers (506, FIG. 5) have been cut from the electrode pads (512, FIG. 5), the electrode pads remain fastened to the sacrificial substrate (502). The tethered set (500) of winged tabs is aligned over the electrode pads so that a base portion (520) overlies each electrode pad (512, FIG. 5). The position of the underlying electrode pads is illustrated by the dashed line (522). A variety of methods could be used to connect the tethered set (500) of winged tabs to the electrode pads (512), including resistance or laser spot welding.

The dashed trapezoid illustrates the wing portions (525), which will be folded up to contain the wires. The wings (525) may have several additional features, such as holes (515). According to one illustrative embodiment, during a later manufacturing step, a fluid matrix such as liquid silicone rubber is injected into a mold which contains the electrodes and their associated wiring. The fluid matrix flows through the holes (515), and then cures to form the flexible body. The holes (515) provide a closed geometry through which the fluid matrix can grip the electrode assembly.

A second dashed rectangle outlines a tab (530), which will be folded over a wire and welded to mechanically secure it to the electrode. This wire provides electrical energy to the electrode. The spacing (535) of the winged tabs (513) along the rails (505) matches the pitch of the underlying electrode pads (512, FIG. 5). The pitch of the electrode pads (512, FIG. 5) and the winged tabs (513) is also the pitch of the completed electrode assemblies in the final electrode array.

One or more welds (524) are made to join each of the winged tabs (513) to the underlying electrode pads (512, FIG. 5). A thin coating of silicone or other biocompatible insulating material can be deposited over an inner surface of the electrodes and wings and cured. This silicone layer provides a compliant and electrically insulating layer between the wires and the electrodes. The silicone layer can prevent mechanical abrasion and/or electrical shorting of the wires. According to one illustrative embodiment, the wires are also individually insulated. For example, the wires may be individually insulated by a parylene coating. The tethers (510) are then cut and the tethers and rails (505) are removed.

Figure 7A:
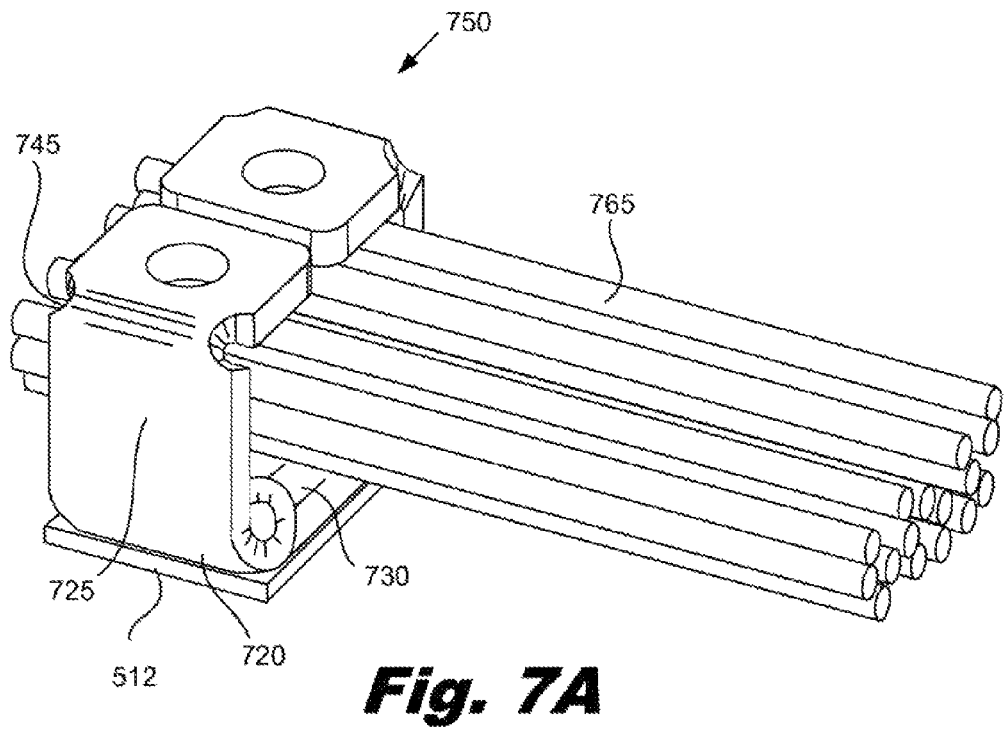
FIGS. 7A and 7B are a perspective and cross-sectional view, respectively, of one illustrative embodiment of a composite electrode assembly having an integral wire carrier, according to one embodiment of principles described herein.

FIG. 7A is a perspective diagram of an illustrative composite electrode assembly (750) which forms an integral wire carrier. The overall size of the finished electrode assembly (750) may be on the order of millimeters or less than a millimeter, with feature sizes on the order of tens to hundreds of microns. To form the electrode assembly, the flap (730) of the winged tab is folded over a selected wire and welded to electrically and mechanically secure the wire to the winged tab. The wings (725) are bent in two locations, once near the base (720) and again at the notches (745) to form a rectangular wire carrier around the wires (765). In its folded form, the winged tab forms a support structure which is both a wire carrier (780) and a support to the underlying electrode pad (512).

Figure 7B:
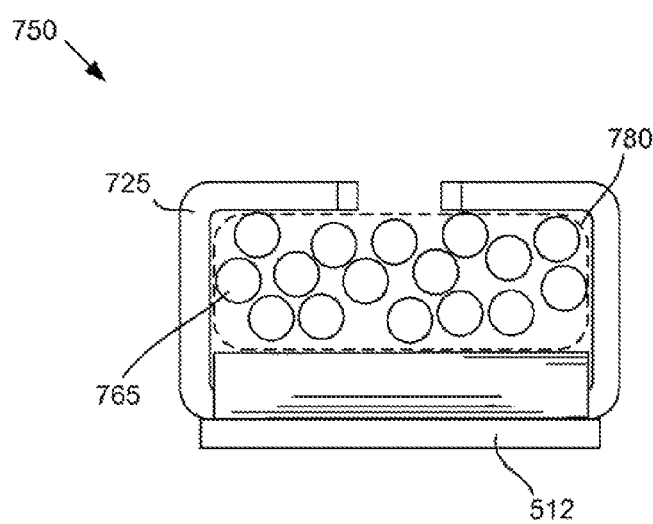

FIG. 7B is a cross sectional diagram of the composite electrode assembly (750) shown in FIG. 7A. As discussed previously, the electrode pad (512) is on the underside of the electrode assembly (750). The electrode pad (512) may have a thickness which is equal to, less than, or greater than the thickness of the flexible conductive material which makes up the winged tab. In general, the electrode pad (512) may have any thickness suitable to a desired application.

According to one illustrative embodiment, all of the electrode assemblies for a single cochlear implant are machined from the two sheets of conductive material, one flexible sheet of material and the other high charge transfer sheet of material. For example, the electrode pads and winged tabs can be machined from a flexible sheet of conductive material at their desired spacing in the cochlear lead and be held in place to an outer frame by small tethers. The winged tabs can be formed with a number of features that facilitate the final assembly of the cochlear lead. As discussed above, precision short pulse laser machining and automated alignment of the components can reduce the amount of manual work required and improve yields.

Figure 8A:
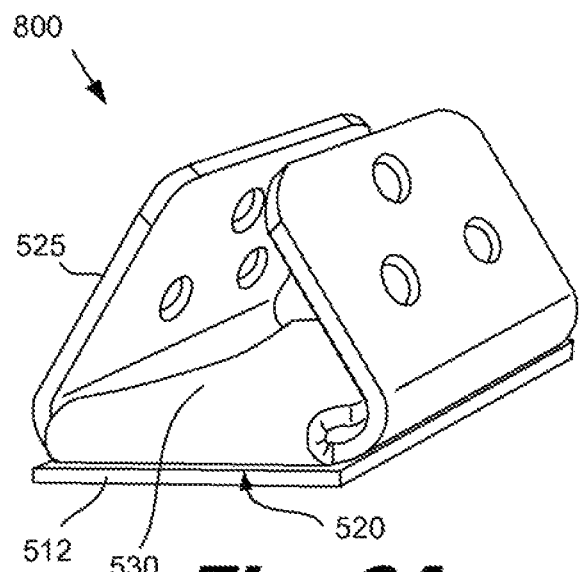
FIGS. 8A and 8B are a perspective and cross-sectional view, respectively, of one illustrative embodiment of a composite electrode assembly having an integral wire carrier, according to one embodiment of principles described herein.

FIG. 8A is a perspective view of another illustrative embodiment of a composite electrode assembly (800), which includes an integral wire carrier and an electrode pad (512) welded on the bottom of the folded winged tab. For clarity of illustration, the wires are not shown in FIG. 8A. As discussed above, the tab (530) is folded over the wire associated with this composite electrode assembly (800) and welded to electrically and mechanically secure it in place. The wings (525) are folded up to secure the wires for the more distal electrodes and form a bundle of wires which passes back along the electrode array to the cochlear lead and to the internal processor. The electrode pad (512) is on the underside (520) of the folded tab (530). The electrode pad (512) is not covered by the flexible body and is consequently exposed to the body tissues and fluids within the cochlea. The activated surface of the electrode pad (512) transfers electrical charge from the connected wire to the tissues. As discussed above, the electrode pad (512) may be formed from a variety of materials. According to one illustrative embodiment, the electrode pad (512) has an activated iridium oxide layer on its external surface. The activated iridium oxide layer may have a charge transfer capability of approximately 3 to 7 mC/cm^2. This charge transfer is significantly greater than a smooth platinum surface which typically has a charge transfer capability of approximately than 1 mC/cm^2. The transferred charge creates an electrical field through the surrounding tissues, thereby stimulating the adjacent auditory nerve.

Figure 8B:
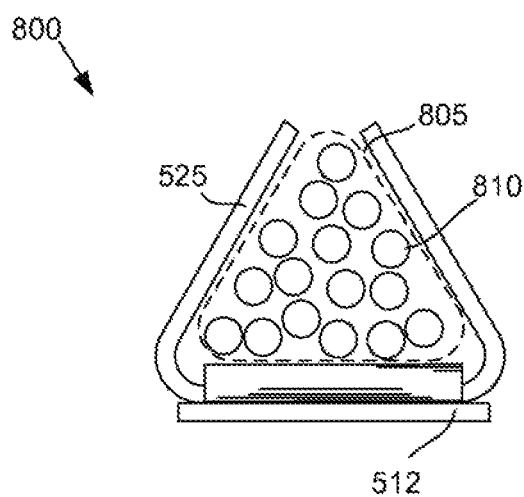

FIG. 8B is a cross-sectional view of the composite electrode assembly (800) shown in FIG. 8A. Cross-sections of the wires (810) are shown in a wire bundle (805) contained by the wings (525). As discussed above, this wire bundle (805) passes through the entire length of the electrode array (195, FIG. 3); however, each individual wire within the bundle terminates at the electrode to which it is welded.

Figure 9:
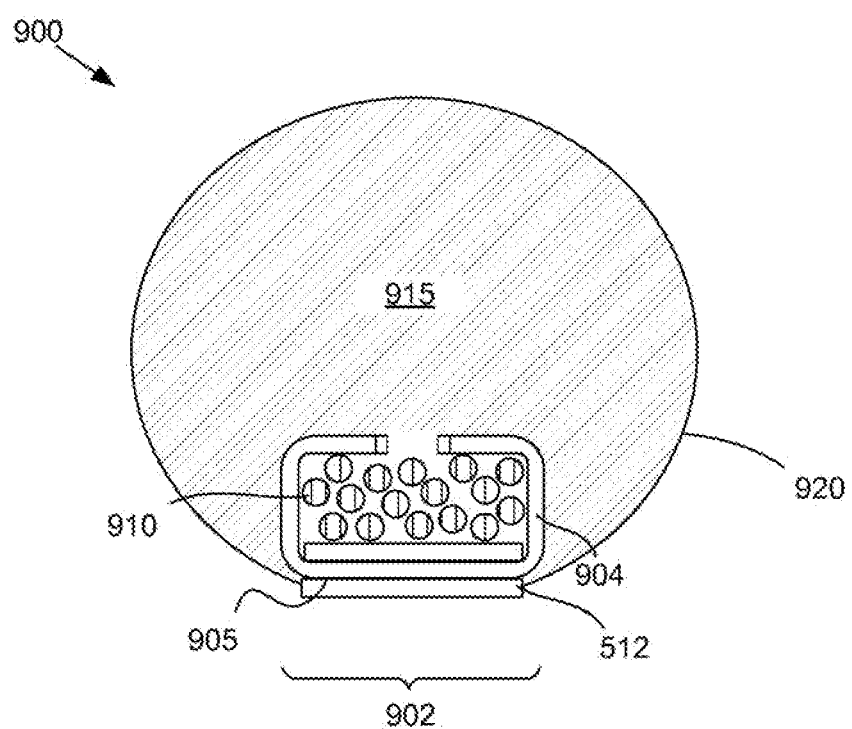
FIG. 9 is a cross-sectional view of an illustrative cochlear lead having an electrode pad exposed at an outer surface of a flexible body of the cochlear lead, according to one embodiment of principles described herein.

FIG. 9 shows a cross-sectional view of a cochlear electrode (900). A composite electrode assembly (902) on a wire bundle (910) is partially embedded in the flexible body (915). The composite electrode assembly (902) includes a support structure (904) and an electrode pad (512) which is attached to the bottom surface (905) of the support structure (904). According to one illustrative embodiment, the partial encapsulation of the composite electrode assembly (902) is performed using a mold and a liquid injection molding process. The composite electrode assembly (900) is positioned in the mold and the mold is closed. A curable liquid, such as a medical grade liquid silicone rubber, is then injected into the mold. After encapsulation, the curable liquid (920) is then cured and the assembly is removed from the mold.

The curable liquid fills voids within the composite electrode assembly (902) and entirely encapsulates it except for one surface of the electrode pad (512). This allows the electrode pad (512) of each composite electrode assembly (902) to contact the tissue in the cochlea where each electrode is located after inserting the lead into the cochlea. The high charge transfer at the surface of the electrode pad (512) provides for more efficient stimulation of the cochlear tissue than if the conductive material of the winged tab were used as the stimulating surface.

Figure 10:
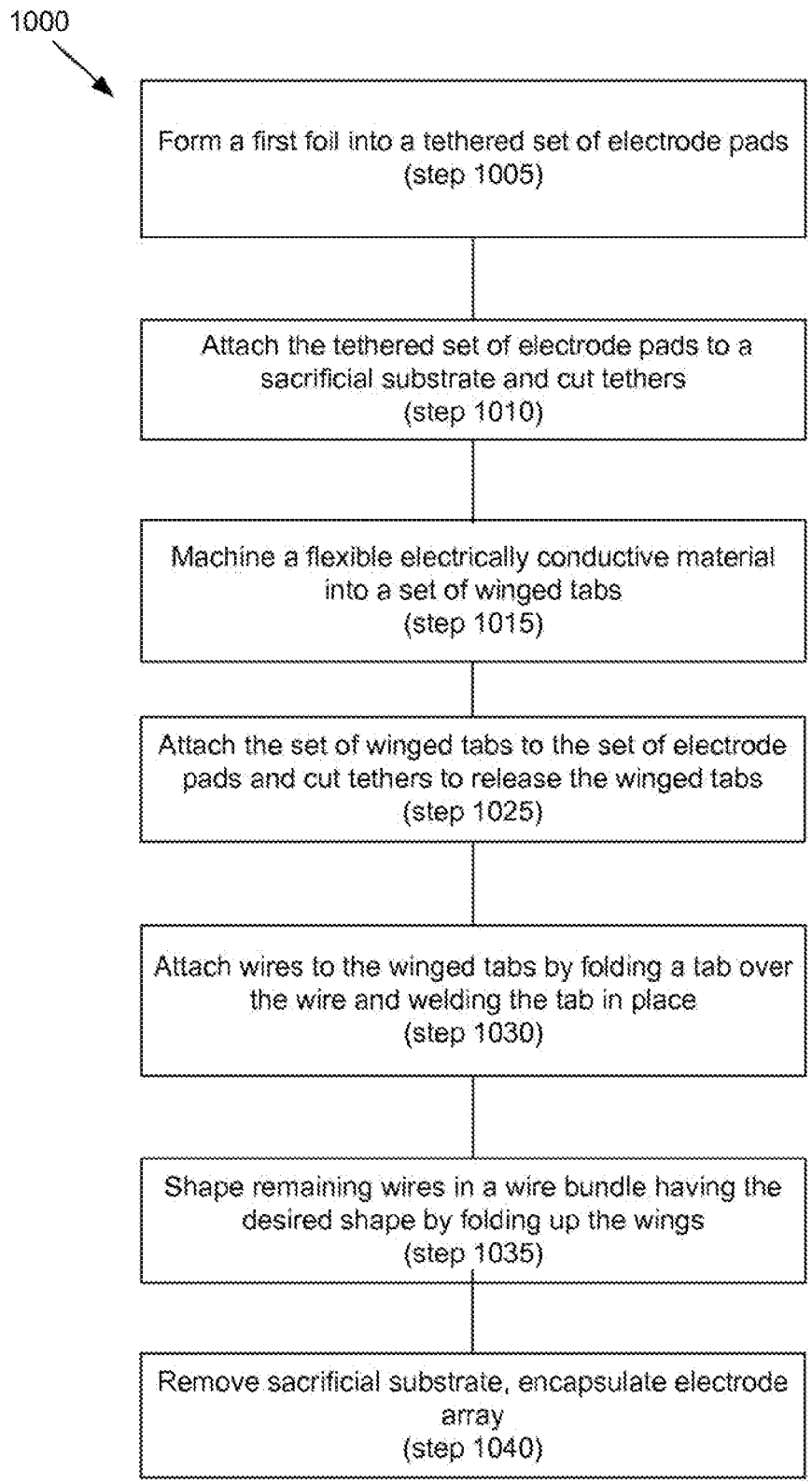
FIG. 10 is a flowchart diagram of an illustrative method for forming an electrode array, according to one embodiment of principles described herein.

FIG. 10 shows a flowchart (1000) of a method forming a cochlear electrode array. The method includes forming a first foil into a tethered set of electrode pads (step 1005). The tethered set of electrode pads is mechanically attached to a sacrificial substrate and the tethers are cut (step 1010). A second foil of flexible electrically conductive material is formed into a tethered set of winged tabs (step 1015). The tethered set of winged tabs is then attached to the electrode pads and the tethers cut to release the winged tabs (step 1025). The appropriate wires can then be connected to the corresponding electrode assemblies. According to one illustrative embodiment, the wire is attached to the winged tabs by folding a tab over the wire and welding the tab in place to hold the wire (step 1030). The remaining wires are shaped into the desired wire bundle geometry by folding up the wings (step 1035). The sacrificial substrate can then be removed and the electrode array encapsulated in a flexible polymer body (step 1040). In embodiments where the sacrificial substrate is an iron strip, the iron strip can be removed using a selective acid etch. The oxidization etch is tailored such that the iron strip is removed, but the materials of the electrode assembly are not affected.

Figure 11:
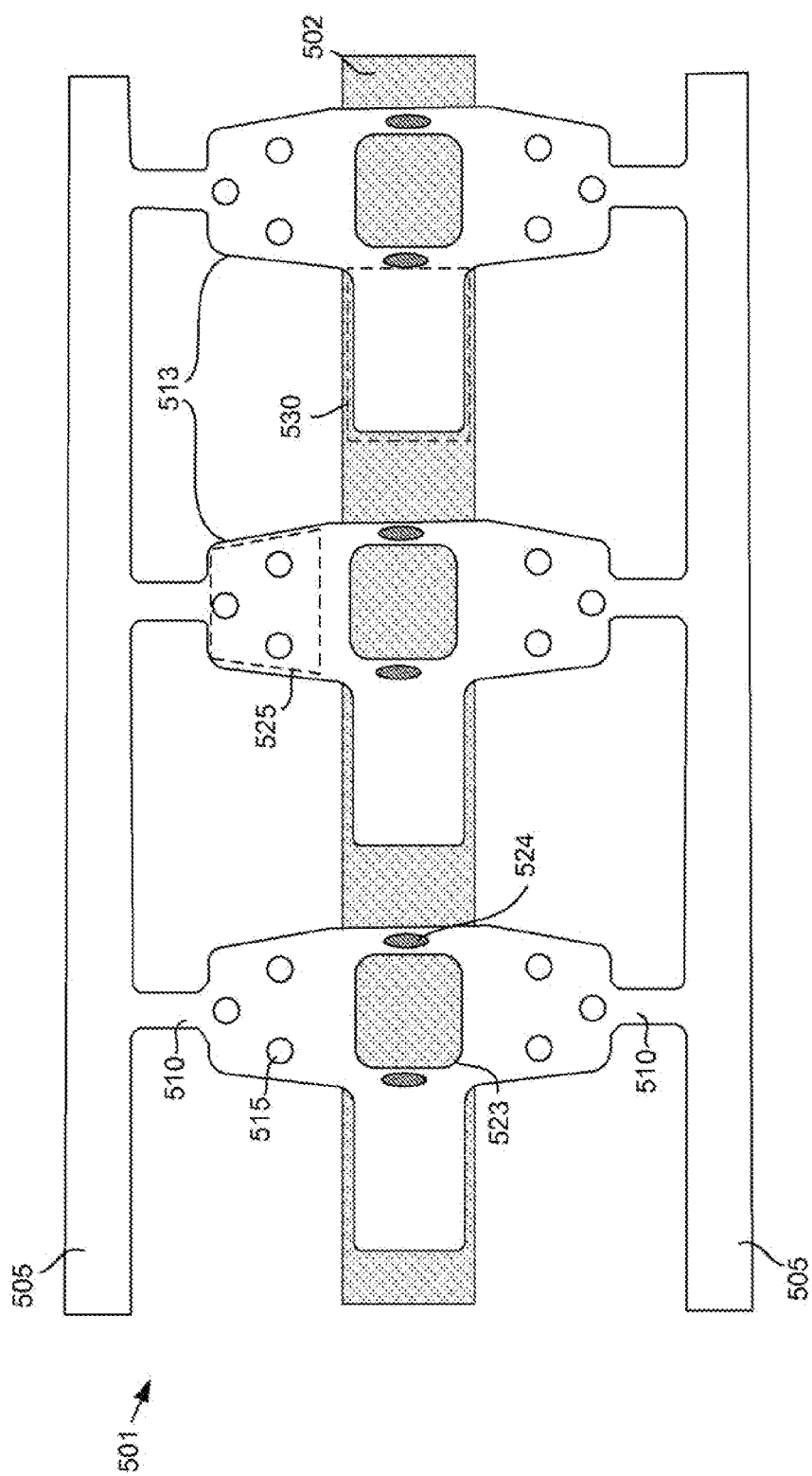
FIG. 11 is a top view of a patterned sheet of flexible conductive material which is attached to a sacrificial substrate, according to one embodiment of principles described herein.
Figure 12:
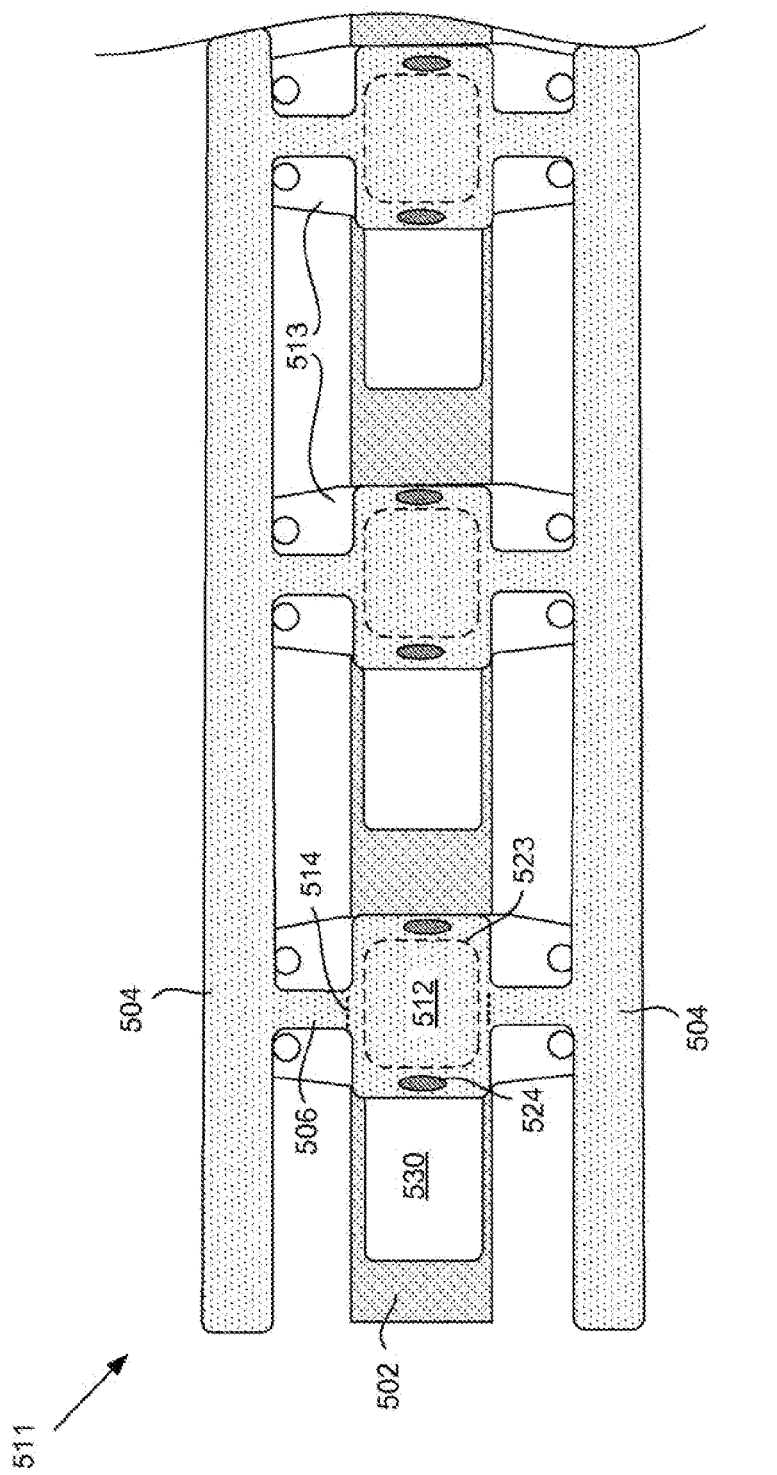
FIG. 12 is a top view of a patterned sheet of electrochemically activated material attached over apertures in a flexible conductive material, according to one embodiment of principles described herein.
Figure 13:
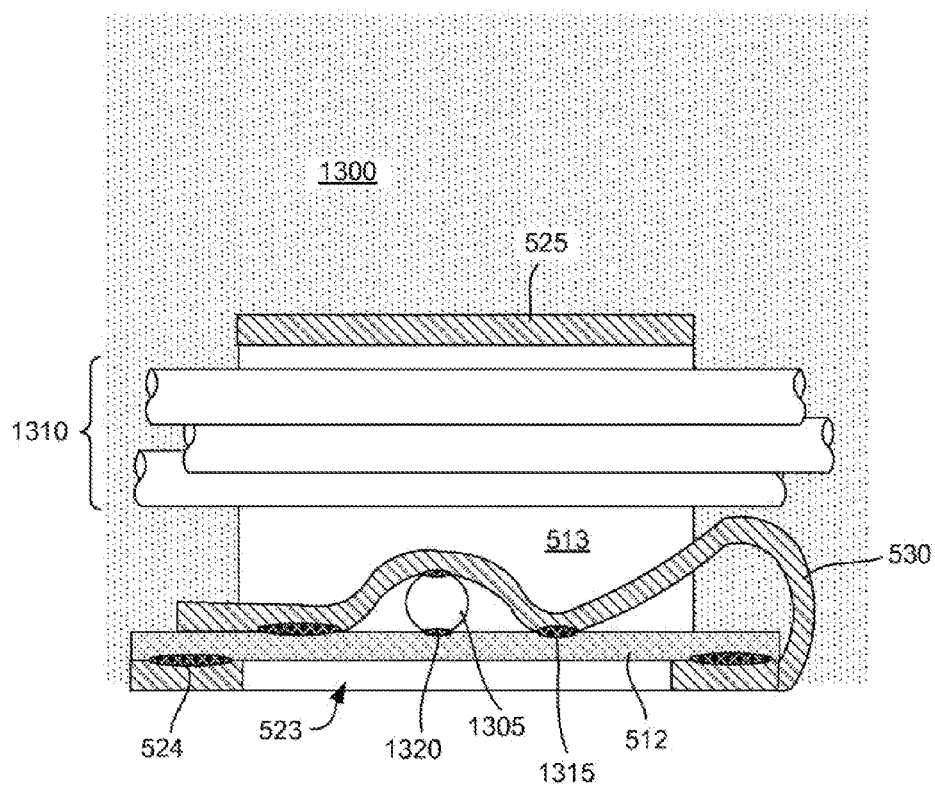
FIG. 13 is a cross sectional view of an electrode assembly which is encapsulated in a flexible body, according to one embodiment of principles described herein.

FIGS. 11, 12 and 13 describe an alternative method for creating a cochlear electrode array. FIG. 11 is a diagram showing a tethered set (501) of winged tabs being attached to a sacrificial strip (502). In this embodiment, the tethered set (501) of winged tabs (513) is similar to that which was previously described in FIG. 6. One significant difference is that a central portion of the winged tabs (513) has been removed to form a window or central aperture (523) in each winged tab (513). The central aperture (523) is formed in the base portion of the winged tabs (513). According to one illustrative embodiment, the size of the central aperture (523) is maximized while retaining sufficient mechanical strength in the winged tabs (513) to support the wings (525) and tab (530). As discussed above, the tethered set (501) of winged tabs can be attached to the sacrificial strip (502) using a variety of methods including weld joints (524). The tethers (510) can then be cut or broken to free the winged tabs (513), which are then held in place by the sacrificial strip (502) and weld joints (524).

FIG. 12 is a diagram which shows an illustrative tethered set (511) of electrode pads being joined to the winged tabs (513). As discussed above, the set of electrodes could be formed from a material which has a relatively high charge transfer from the electrode pads (512) into the surrounding tissues and fluids of the cochlea. According to one illustrative embodiment, the electrode pads (512) could be formed from iridium which has a layer of activated iridium oxide. As discussed above, the electrode pad (512) has an activated iridium oxide layer on its external surface. The charge transfer of the activated iridium oxide layer is significantly greater than a smooth platinum. Charge transfers from the iridium oxide layer as high as 40 mC/cm^2 are possible, but charge transfers at this level could irreversibly damage the iridium oxide layer. Without being bound to any particular theory, it appears that iridium oxide films inject charge via reversible reduction and oxidization between $Ir^{3+}/Ir^{4+}$ valance states.

The tethered set (511) of electrode pads is aligned with the winged tabs (513) and then fastened in place. As discussed above, one method of fastening the winged tabs (513) and the electrodes together is resistance or laser spot welding. The tethers (506) can then be cut or broken along the dashed line (514).

Although a sacrificial strip (502) is illustrated as a means for holding the winged tabs (513) and electrode pads (512) in place, a wide variety of other techniques could be used. For example, the winged tabs (513) and/or electrode pads (512) could be placed on an adhesive surface. The adhesive surface would hold the various components in place through the assembly process. The adhesive surface could then be removed mechanically or chemically. For example, a solvent such as acetone or isopropyl alcohol could be used to facilitate the removal of the adhesive surface. Additionally or alternatively, a wax or other compliant surface could be used to hold the various components in place. For example, the winged tabs could be pressed into a wax surface or other deformable surface. After the assembly process, the wax could be removed by heating.

FIG. 13 shows a cross sectional diagram of the illustrative electrode assembly illustrated in FIGS. 11 and 12 after the assembly and encapsulation processes are complete. As was previously discussed, the electrode pad (512) may be joined to a winged tab (513) by weld joints (524). The electrode pad (512) covers the central aperture (523) in the winged tab (513). One of the tabs (530) is folded over a designated wire (1305). This brings the wire (1305) into direct contact with the electrode pad (512). The wire (1305) may be secured in a number of ways including forming additional weld joints (1315) between the folded tab (530) and the electrode pad (512). Additionally or alternatively, weld joints (1320) can be made which directly electrically attach the wire (1305) to the electrode pad (512) and/or the overlying tab (530).

After the designated wire (1305) is secured in place, the wings can be folded up to form a wire bundle (1310) which contains the wires which continue through the cochlear electrode array to provide current to other electrodes. The sacrificial substrate can then be removed and the entire electrode array can be partially encased in a silicone rubber body (1300), leaving the outer surface of electrode pad (512) exposed through the central aperture (523).

This alternative method may have a number of advantages. For example, the electrode surface is somewhat recessed, which may protect it from damage. Additionally, because the electrode pads are not welded to the sacrificial strip and are not bent during the assembly process, more fragile surface layers can be used on the electrode pads to improve the charge transfer of the electrode.

Figure 14:
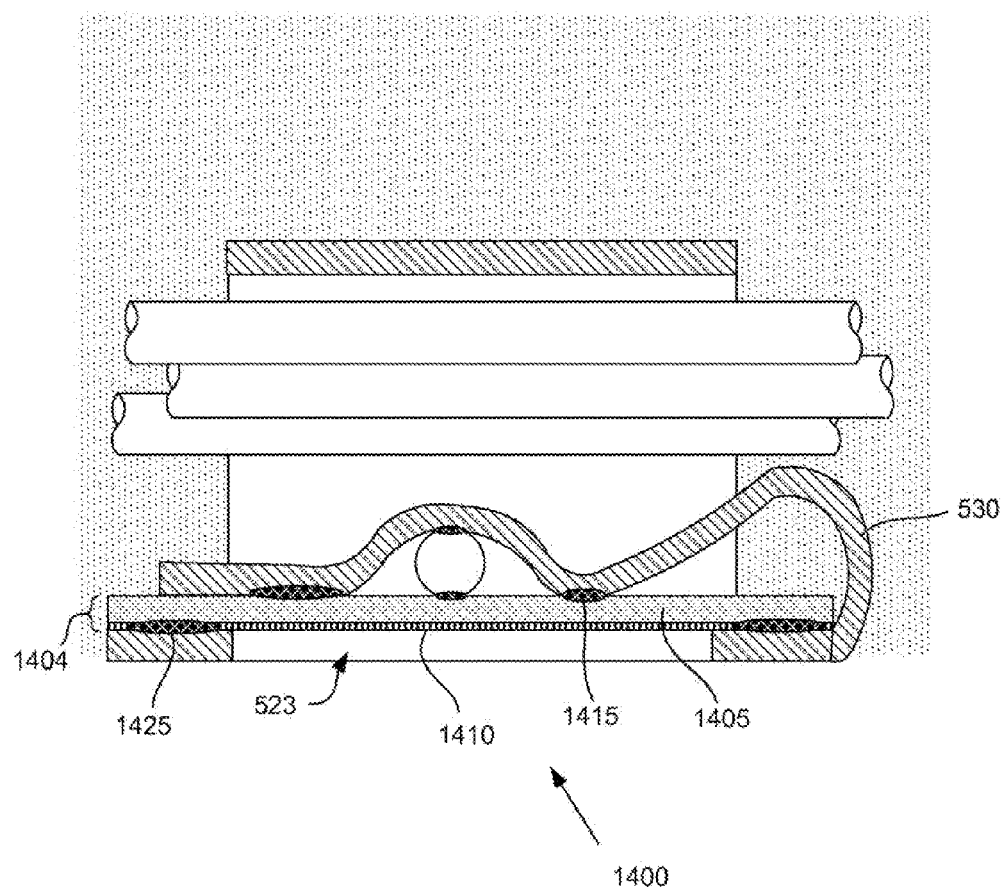
FIG. 14 is a cross sectional view of an electrode assembly which includes a surface layer on an electrode pad, according to one embodiment of principles described herein.

FIG. 14 is a cross sectional diagram of a cochlear electrode (1400), which includes an electrode substrate (1405) that has a surface layer (1410) which increases its charge transfer capability. Together, the electrode substrate (1405) and surface layer (1410) form the electrode pad (1404). According to one illustrative embodiment, the surface layer (1410) can increase the charge transfer capability of the cochlear electrode (1400) primarily by increasing the surface area compared to smooth platinum. This can be done by "activating" a surface of the electrode pad (1404) or by depositing a coating on the surface of the electrode pad (1404). Examples of depositing a coating on the surface of the electrode pad (1404) may include depositing a thin film such as sputtered iridium oxide, titanium nitride, ruthenium oxide, porous niobium oxide, or activated carbon. Other examples of structures which increase the surface area of the electrode pad (1404) include depositing or forming platinum grey, platinum black, sintered platinum, nanostructures, or other appropriate structures which have high surface areas on the electrode substrate (1405). As described in U.S. Pat. Nos. 6,974,533 and 5,751, 011, platinum gray refers to a platinum microstructure which has a significantly larger surface area than smooth platinum and forms a relatively strong and adhesive film.

Platinum black is a fine powder of platinum which can be deposited over a solid platinum substrate. This process produces a surface area which is much higher than the geometric surface area of the underlying substrate and exhibits charge transfer characteristics which are superior to non-textured platinum surfaces. The platinum particles are typically sprayed or hot pressed onto the substrate layer. According to one illustrative embodiment, platinum black may be electroplated onto a platinum substrate. The platinum substrate is first cleaned, and then placed in a water solution which contains chloroplantanic acid and lead acetate. An electrical current is then passed through the water solution such that chlorine evolves at the anode and deposits platinum black particles on the platinum substrate.

While iridium oxide films are known to have charge transfer characteristics which are superior to most forms of platinum, the iridium oxide films are also known to be brittle and have delaminating problems when the underlying surface is bent. To avoid this, the films and structures described above could be deposited on the electrode substrate (1405) which is not required to flex during the manufacture or use of the electrode array.

Many of these films and structures could be damaged if they were directly deposited or produced on a winged tab which is then folded into the electrode/wire carrier configuration. For example, structured platinum, such as platinum black, platinum gray, sintered platinum, platinum nanoparticles, and platinum metal sponges can all be sensitive to folding or welding of the underlying substrate, tending to crack or delaminate from the substrate.

According to one illustrative embodiment, the electrode pad (512) may be a layer that is deposited directly on the bottom of the winged tab rather than on a separate piece of material. For example, the electrode pad (512) may be formed by depositing iridium on the base of a platinum winged tab. This deposition could be carried out by electroplating, electroless plating, sputter coating, vapor phase deposition, pulsed laser deposition, or other suitable methods. According to one illustrative embodiment, an iridium oxide film is sputtered onto the surface using DC reactive sputtering from an iridium metal target in an oxidizing environment. The thickness of the sputtered film may be from about 100 nanometers to several microns. This can result in a charge-injection capacity which is between 1 and 9 mC/cm^2, which is comparable to an activated iridium oxide electrode pad. Additionally or alternatively, an iridium film may be deposited onto the surface and subsequently activated as described above.

According to one illustrative embodiment, iridium oxide nanoparticles could be joined to form a high surface area layer (1410) over the electrode substrate (1405). A wide variety of iridium oxide nanoparticles could be used, including nanoparticles which are spherical, faceted, nanorods, nanowhiskers, nanopyramids, and other shapes. Iridium oxide nanoshapes with a size between 20 and 80 nanometers can have a surface area of 10 to 50 square meters per gram. Larger nanoshapes which have a size of 100 nanometers can have surface areas of approximately 7 to 10 square meters per gram. These high surface areas, combined with the intrinsically high charge transfer characteristics of the iridium oxide can produce an electrode with a very high rate of charge transfer. These iridium oxide nanoparticles could be joined by sintering, embedding in a matrix, or by other means. In other embodiments, the iridium oxide nanoparticles could be grown directly on an iridium oxide substrate.

A variety of techniques and materials can be used to improve the mechanical and electrical properties of the thin films and structures. According to one illustrative embodiment, an iridium oxide thin film is deposited over a roughened platinum surface. For example, a platinum gray layer may be deposited over the platinum substrate (1405). This produces a microporous structure over the platinum which has good adhesion to the underlying platinum substrate. An iridium oxide thin film layer may then be deposited over the high surface area platinum gray layer. Because the iridium oxide thin film is deposited on a textured surface, its surface area and its adhesion to the surface is increased.

Additionally or alternatively, the adhesion of a sputtered iridium oxide layer may be improved by initially sputtering a combination of platinum and iridium oxide onto a platinum substrate (1405), and then gradually changing the composition to include more iridium oxide until only iridium oxide is deposited. This graduated coating may improve the adhesion and charge transfer between the platinum substrate (1405) and the iridium layer (1410).

As described above in FIGS. 11-13, the electrode pad (1405) may be joined to a winged tab (513, FIG. 12) by weld joints (1425). Although forming the weld joints (1425) may damage the thin film or structure of the surface layer (1410) in the weld joint region, this will not impair the structure or overall charge transfer of the portion of the surface layer (1410) that is exposed to the cochlea through the window (523). The assembly process then proceeds as previously described. A tab (530) is folded over a designated wire and the tab (530) and the wire are welded in place. The resistance or laser welding process is adjusted so that the welds (1415) join the tab (530) and wire to the electrode pad (1405) without disrupting the surface layer (1410).

Figure 15:
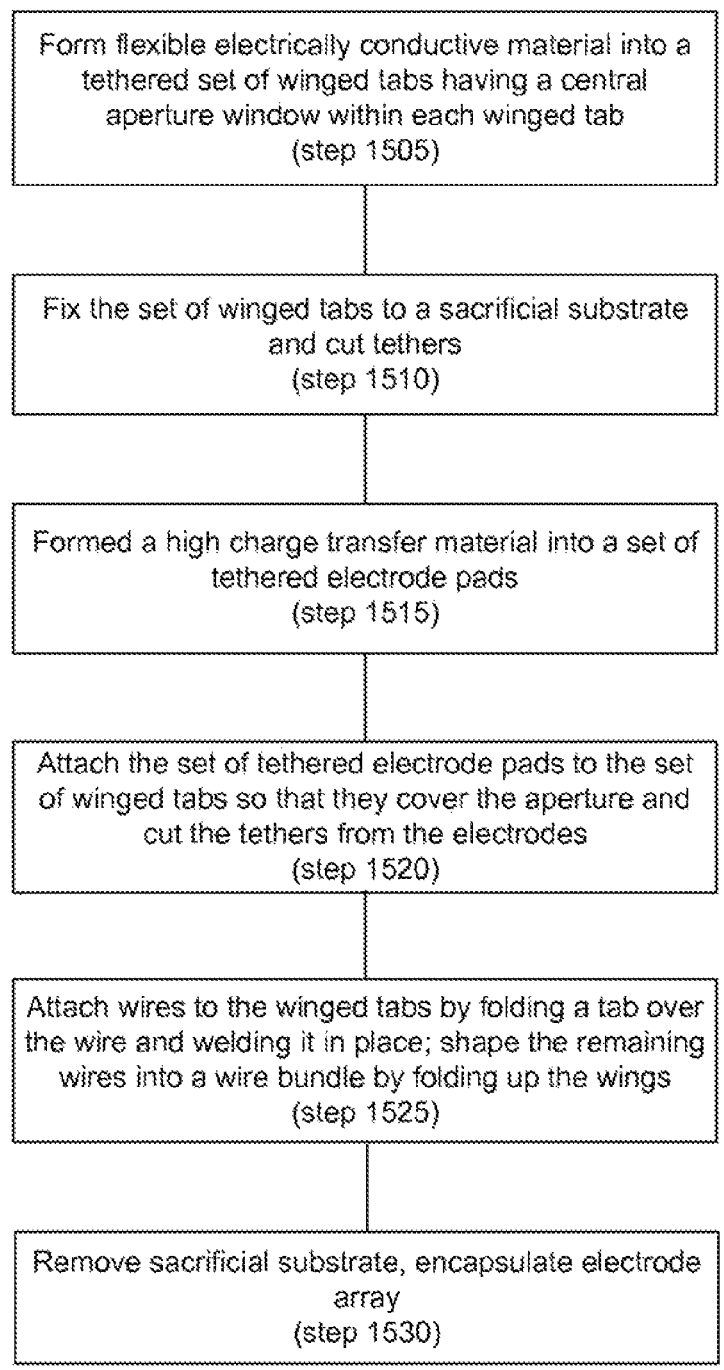
FIG. 15 is a flowchart showing one illustrative method for forming an electrode in a cochlear electrode array, according to one embodiment of principles described herein.

FIG. 15 is a flowchart which shows one illustrative method (1500) for forming a cochlear electrode array. According to one illustrative embodiment, a flexible electrically conductive material is formed into a tethered set of winged tabs which have a window within each winged tab (step 1505). As discussed above, the flexible electrically conductive material may be platinum or a platinum alloy. The tethered set of winged tabs is fixed to a sacrificial substrate and the tethers are cut (step 1510). A high charge transfer material is formed into a set of tethered electrode pads. For example, the high charge transfer material may be an iridium based material and the forming process may be short pulse laser machining.

The tethered set of electrode pads is attached to the set of winged tabs such that an electrode pad covers the central aperture in each winged tab and the tethers are cut from the electrode pads (step 1520). The wires are attached to the winged tabs by folding a tab over a selected wire and welding the wire in place. The remaining wires are formed into a bundle by folding up the wings (step 1525). This process is repeated for each electrode assembly in the array until all of the wires are connected to an electrode pad and properly formed into the wire bundle. The sacrificial substrate can then be removed and the electrode array encapsulated (step 1530).

The process described above is only one illustrative method for forming a cochlear electrode array. The steps may be performed in a variety of orders and a number of additional steps may be used. For example, step 1515 can occur any time before step 1520. Additional steps, such as surface preparation, testing, or other steps, can be included in the process.

The preceding description has been presented only to illustrate and describe embodiments and examples of the principles described. This description is not intended to be exhaustive or to limit these principles to any precise form disclosed. Many modifications and variations are possible in light of the above teaching.

The invention claimed is:

1. A cochlear lead comprising:
   a flexible body;
   a plurality of electrode assemblies partially embedded in the flexible body, the plurality of electrode assemblies being configured to stimulate an auditory nerve from within a cochlea, each of the electrode assemblies comprising:
   a support structure comprising flexible electrically-conductive material comprising a central aperture and two wing tabs disposed on opposite sides of the central aperture, wherein the two wing tabs are folded toward each other to partially surround the electrical connections running along the flexible body to each of the electrode assemblies; and
   an electrical pad disposed on the support structure between the two wing tabs and positioned to contact cochlear fluids and tissues through the central aperture, in which an exterior surface of the pad exposed to cochlear fluid and tissue is a different material or morphology than the electrode assemblies.

2. The cochlear lead according to claim 1, in which the flexible electrically conductive material comprises platinum.

3. The cochlear lead according to claim 1, in which a surface of the electrode pad comprises activated iridium oxide.

4. The cochlear lead according to claim 1, in which the support structure further comprises a third tab, in addition to the two wing tabs, the third tab being folded over the central aperture to hold the electrode pad between the folded third tab and the central aperture.

5. The cochlear lead according to claim 1, in which the electrode pad is attached to the flexible electrically conductive material with a resistance weld.

6. The cochlear lead according to claim 1, in which the electrical connections comprise a bundle of wires in which the support structure and folded wing tabs of each electrode assembly define a boundary in which the bundle of wires is disposed.

7. The cochlear lead of claim 4, in which the folded third tab secures an electrical connector in electrical connection with the electrode pad.

8. The cochlear lead of claim 1, where a wing tab has multiple bends in it.

9. The cochlear lead of claim 1, where a wing tab has one or more holes in it.

10. A method for forming the cochlear lead of claim 1, the method, comprising:
    forming a first foil of flexible electrically conductive material into a set of support structure each have a central aperture and two wing tabs;
    forming a second foil into a set of electrode pads;
    fixing a sacrificial substrate to one of: the support structure and the electrode pad;
    attaching the set of support structures and the set of electrode pads together; and
    electrically connecting a select wire to each of the electrodes pads.

11. The method according to claim 10, further comprising:
    removing the sacrificial substrate to form the plurality of electrode assemblies; and
    partially encapsulating the electrode assembly in a flexible body.

12. The method according to claim 10, in which forming the first and second foil comprises short pulse laser machining.

13. The method according to claim 10, in which forming the first foil comprises formed a tethered set of supports structures with wing tabs and forming a second foil comprises forming a tethered set of electrode pads.

14. The method according to claim 13, further comprising cutting tethers of a tethered set of support structures after attaching the support structures and the electrode pads together.

15. The method according to claim 10, further comprising electrochemically activating an iridium material of the electrode pads by subjecting a surface of the iridium material to a number of electrochemical cycles in a water-based electrolyte such that the surface of the iridium material develops an activated iridium oxide layer which has electrical charge transfer which is superior to the first foil.

16. A cochlear electrode array comprising:
    a flexible body;
    a plurality of electrode assemblies partially embedded in the flexible body, the plurality of electrode assemblies being configured to stimulate an auditory nerve from within the cochlea, each of the electrode assemblies comprising:
    a flexible electrically conductive material forming a support structure; and
    an electrode pad attached to the flexible electrically conductive material, wherein, with respect to the flexible body in which the electrode assemblies are partially embedded, a portion of both the support structure and the electrode pad are electrically exposed to cochlear fluids and tissues, in which the electrode pad has an exposed surface have a charge transfer to cochlear fluids and tissues that is higher than that of exposed portions of the flexible electrically-conductive material of the support structure.

17. The cochlear lead of claim 16, where a wing tab has multiple bends in it.

18. The cochlear lead of claim 16, where a wing tab has one or more holes in it.

19. A cochlear lead comprising:
    a flexible body;

a plurality of electrode assemblies partially embedded in the flexible body, the plurality of electrode assemblies being configured to stimulate an auditory nerve from within a cochlea, each of the electrode assemblies comprising:

a support structure comprising flexible electrically-conductive material comprising a central aperture and two wing tabs disposed on opposite sides of the central aperture, wherein the two wing tabs are folded toward each other to partially surround the electrical connections running along the flexible body to each of the electrode assemblies; and an electrical pad disposed on the support structure between the two wing tabs and positioned to cover the central aperture and contact cochlear fluids and tissues through the central aperture wherein, with respect to the flexible body in which the electrode assemblies are partially embedded, a portion of both the support structure and the electrode pad are electrically exposed to cochlear fluids and tissues, in which the electrode pad has an exposed surface having a charge transfer to the cochlear fluids and tissues that is higher than that of exposed portions of the flexible electrically-conductive material of the support structure.

20. The cochlear lead of claim 19, where a wing tab has multiple bends in it.

21. The cochlear lead of claim 19, where a wing tab has one or more holes in it.

* * * * *